United States Patent [19]

Beevor

[11] Patent Number: 4,788,338
[45] Date of Patent: Nov. 29, 1988

[54] PREPARATION OF KETONES

[75] Inventor: Robert G. Beevor, Twickenham, England

[73] Assignee: The British Petroleum Company p.l.c., London, England

[21] Appl. No.: 61,105

[22] Filed: Jun. 12, 1987

[30] Foreign Application Priority Data

Jun. 19, 1986 [GB] United Kingdom ............... 86 14910

[51] Int. Cl.$^4$ .............................................. C07C 45/49
[52] U.S. Cl. ................................................... 568/387
[58] Field of Search ....................................... 568/387

[56] References Cited

U.S. PATENT DOCUMENTS

| | | | |
|---|---|---|---|
| 3,059,031 | 10/1962 | Alderson | 568/387 |
| 3,257,459 | 6/1966 | Swakon et al. | 568/387 |
| 3,697,600 | 10/1972 | Fenton | 568/387 |
| 3,829,499 | 8/1974 | Noyaki | 568/387 |
| 3,857,893 | 12/1974 | Noyaki | 568/387 |
| 3,923,904 | 12/1975 | Hara | 568/387 |
| 4,602,116 | 7/1986 | Cooper | 568/387 |

FOREIGN PATENT DOCUMENTS 827396  2/1980  United Kingdom ............... 568/387

OTHER PUBLICATIONS

Isnard et al., J. Organometalic Chem., vol. 240, pp. 169–177 (1982).

*Primary Examiner*—James H. Reamer
*Attorney, Agent, or Firm*—Nixon and Vanderhye

[57] ABSTRACT

A process for preparing ketones comprises reacting an alkene with carbon monoxide and a secondary alcohol at elevated temperature in the presence of a rhodium catalyst and an aminoalcohol or aminoether promoter. A preferred catalyst is $Rh_6(CO)_{16}$ and a preferred promoter is $N(CH_2CH_2OCH_2CH_2OCH_3)_3$.

7 Claims, No Drawings

PREPARATION OF KETONES

The present invention relates to a process for the preparation of ketones by carbonylation of alkenes in non-aqueous hydrogen donor solvents.

The carbonylation of alkenes in the presence of non-aqueous hydrogen donor solvents to yield ketones is described in GB Pat. No. 827,396. In this reference it is disclosed that a rhodium-containing material is an effective catalyst.

Journal of Organometallic Chemistry 240 (1982) p 169–177 describes an improvement of the process described above wherein a base promoter is used in conjunction with a rhodium catalyst. Examples of bases disclosed in this reference are simple amines such as trimethylamine and tristhylamine.

It has now been discovered that the carbonylation of an alkene in the presence of a non-aqueous hydrogen donor solvent can be further improved if the base promoter described above is replaced by either an aminoalcohol or an aminoether. Use of an aminoalcohol or aminoether promoter leads to an increase in the rate of reaction and selectivity to the desired ketone relative to the simple amines used in the prior art.

Accordingly, ths present invention provides a process for the preparation of ketones which comprises reacting an alkene with carbon monoxide and a secondary alcohol at elevated temperature in the presence of a rhodium catalyst and, as promoter, an aminoalcohol or aminoether.

The process of the present invention comprises forming one mole of ketone from two moles of alkene, one mole of carbon monoxide and two moles of hydrogen atoms generated from one mole of the secondary alcohol. Thus, if ethylene is the alkene and butan-2-ol is the secondary alcohol, diethyl ketone is produced according to the equation

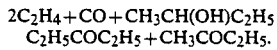
$$C_2H_5COC_2H_5 + CH_3COC_2H_5.$$

The alkene used may in principle be any alkene including mono-, di- and polyolefins. Preferably the alkene is a $C_1$ to $C_6$ mono olefin most preferably either ethylene or propylene.

Any secondary alcohol can in principle be used. Preferred examples include the $C_3$ to $C_{10}$ secondary alcohols particularly butan-2-ol, propan-2-ol, octan-3-ol and the like and $C_5$–$C_{12}$ cyclic alcohols e.g. cyclohexanol, which have secondary hydroxyls are also to be regarded as secondary alcohols.

The carbon monoxide is preferably used in a pure state although minor amounts of gaseous impurities e.g. nitrogen and the inert gases can be present. To avoid the hydroformylation reaction occurring the presence of more than 1% of hydrogen as in the carbon monoxide should be avoided.

The rhodium catalyst may be generated from any convenient rhodium containing source which is soluble under the reaction conditions. Such sources include rhodium halides, rhodium nitrate, acetate and sulphate, rhodium carbonyls and organometallic rhodium complexes.

In addition to the rhodium catalyst, an aminoalcohol or aminoether is used as promoter. The terms aminoalcohol and aminoether, in the context of this patent, are taken to mean organic molecules containing respectively (1) at least one amine group and at least one hydroxyl group and (2) at least one amine group and at least one ether group.

As regards the aminoalcohols these are suitably mono-, di- or trialkanolamines including monoethanolamine, dipropanolamine triethanolamine, N-methylmonoethanolamine and the like. Preferably the aminoalcohol is a trialkanolamine of formula

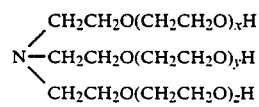

wherein x, y and z are independently zero or integers and the sum of the integers $x+y+z$ is between 3 and 9.

The aminoethers used in the present invention are suitably etherified analogues of the aminoalcohols described above in which at least one of the hydrogens of the hydroxyl groups is replaced by a hydrocarbyl group, preferably a $C_1$ to $C_6$ alkyl group. Preferred aminoethers are those of formula

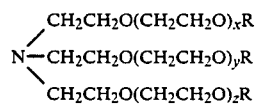

wherein x, y and z are independently zero or integers, the sum of the integers $x+y+z$ is between 3 and 9 and R is either a methyl or ethyl group.

The molar ratio of rhodium to aminoalcohol or aminoether is suitably in the range 6:1 to 1:100 preferably 1:1 to 1:20.

The reaction is preferably carried out at between 150° C. and 23°C. and at a carbon monoxide partial pressure of 40–250 bars. It is preferable to carry out the reaction in the presence of excess secondary alcohol which then functions as both reactant and solvent. The process can be operated either batchwise or continuously.

The invention is now illustrated by the following Examples.

Experimental Details

Butan-2-ol (60 cm$^3$) and catalyst as detailed in the Table were placed in a 300 cm$^3$ stainless steel autoclave fitted with a magnedrive stirrer, thermocouple and cooling coil. This was Purged with carbon monoxide then charged with 20 bar (250 mmol) ethylene and 50 bar CO and heated to 180° C. for 30 minutes. The pressure was maintained at 90 bar by addition of carbon monoxide. After 30 minutes the autoclave was cooled and vented. The liquid and gaseous products were sampled and analysed by gas chromatography.

The results in the Table show that use of either a rhodium/aminoalcohol or a rhodium/aminoether catalyst system results in a substantial improvement in ethylene conversion and selectivity to diethyl ketone relative to either a rhodium catalyst alone (Comparative Tests A and C) or rhodium with a simple amine base (Comparative Test B).

TABLE

| Example/ Comparative Test | Catalyst (mmol) | % C$_2$H$_4$ Conv. | % Selectivity | | | |
|---|---|---|---|---|---|---|
| | | | EtCHO | DEK | Ester[1] | Ethane |
| A | Rh$_6$(CO)$_{16}$ (0.05) | 27.7 | 0.7 | 98.4 | 0.9 | 0 |
| B | Rh$_6$(CO)$_{16}$ (0.05) + Et$_3$N (1.0) | 28.2 | 1.5 | 96.6 | 1.9 | 0 |
| 1 | Rh$_6$(CO)$_{16}$ (0.05) + N(CH$_2$CH$_2$OH)$_3$ (3.0) | 56.3 | 0.7 | 99.0 | 0.3 | Trace |
| 2 | Rh$_6$(CO)$_{16}$ (0.05) + EO$_3$ (3.1)[2] | 47.1 | 0.6 | 99.3 | 0.1 | 0 |
| 3 | Rh$_6$(CO)$_{16}$ (0.05) + EO$_6$ (3.1)[2] | 39.0 | 0.8 | 98.2 | 1.0 | 0 |
| 4 | Rh$_6$(CO)$_{16}$ (0.05) + TDA-1 (3.1)[3] | 70.6 | 0.7 | 98.6 | 0.7 | 0 |
| C | [Rh(OAc)$_2$]$_2$ (0.14) | 35.1 | 0.9 | 97.9 | 1.2 | 0 |
| 5 | [Rh(OAc)$_2$]$_2$ (0.14) + TDA-1 (3.1)[3] | 55.3 | 0.3 | 99.2 | 0.5 | 0 |

[1]Ester: sec-butyl propianate

[2] 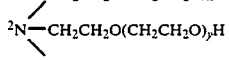 EO$_3$: x + y + z = 3

EO$_6$: x + y + z = 6

[3]TDA-1: Tris(dioxa-3,6-heptyl)amine,N(CH$_2$CH$_2$OCH$_2$CH$_2$OMe)$_3$

I claim:

1. A process for the preparation of ketones, said process comprising reacting an alkene with carbon monoxide and a secondary alcohol at elevated temperature in the presence of a rhodium catalyst and a promoter selected from monoalkanolamines, dialkanolamines, trialkanolamines or etherified analogs thereof.

2. A process as claimed in claim 1, wherein the promoter is a trialkanolamine of formula:

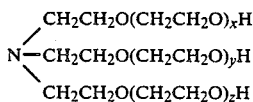

wherein x, y and z are independently zero integers and the sum of the integers x+y+z is between 3 and 9.

3. A process as claimed in claim 1, wherein the promoter is a trialkanolamine of formula:

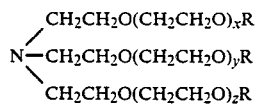

wherein x, y, and z are independently zero or integers; the sum of the integers x+y+z is between 3 and 9 and R is either a methyl or ethyl group.

4. A process as claimed in claim 3, wherein the promoter is N(CH$_2$CH$_2$OCH$_2$CH$_2$OCH$_3$)$_3$.

5. A process as claimed in claim 1, wherein the molar ratio of rhodium to promoter is in the range 1:1 to 1:20.

6. A process as claimed in claim 1, wherein the rhodium catalyst is RH$_6$(CO)$_{16}$.

7. A process for preparation of ketones, which process comprises reacting a C$_1$ to C$_6$ mono-olefin with carbon monoxide and an alcohol selected from the group consisting of C$_3$ to C$_{10}$ secondary alcohols and C$_5$ to C$_{12}$ cyclic alcohols at a temperature in the range of 150° to 230° C. in the presence of a rhodium catalyst and a promoter selected from monoalkanolamines, dialkanolamines, trialkanolamines and etherified analogs thereof.

* * * * *